(12) United States Patent
Cheng et al.

(10) Patent No.: US 7,965,078 B2
(45) Date of Patent: Jun. 21, 2011

(54) METHODS FOR DETERMINING IN SITU THE VISCOSITY OF HEAVY OIL

(75) Inventors: Yuesheng Cheng, Edmonton (CA); Abdel M. Kharrat, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 225 days.

(21) Appl. No.: 12/510,746

(22) Filed: Jul. 28, 2009

(65) Prior Publication Data

US 2010/0033176 A1 Feb. 11, 2010

(30) Foreign Application Priority Data

Aug. 6, 2008 (CA) ..................................... 2638595

(51) Int. Cl.
*G01V 3/00* (2006.01)
(52) U.S. Cl. ........................................ 324/303; 324/300
(58) Field of Classification Search .................. 324/300, 324/303; 73/54.01; 250/269.1
See application file for complete search history.

(56) References Cited

U.S. PATENT DOCUMENTS

| 5,596,274 | A | * | 1/1997 | Sezginer | 324/303 |
| 7,301,339 | B1 | * | 11/2007 | Cheng et al. | 324/303 |
| 7,372,264 | B2 | * | 5/2008 | Akkurt et al. | 324/303 |
| 2010/0039109 | A1 | * | 2/2010 | Cheng et al. | 324/303 |

OTHER PUBLICATIONS

Zittel et al : Reservoir crude-oil Viscosity Estimation from Wireliine NMR Measurements; SPE Annual Technical Conference held in San Antonio, pp. 24-27, Sep. 2006.*

* cited by examiner

*Primary Examiner* — Brij B Shrivastav
(74) *Attorney, Agent, or Firm* — Jay P. Sbrollini; Wayne I. Kanak

(57) ABSTRACT

Viscosity of heavy oil is determined in situ in a formation by making nuclear magnetic resonance (NMR) measurements in the formation, and then calculating viscosity according to an equation of the form $$T_{2LM} = a + b\left(\frac{\eta}{T}\right)^c,$$

where T is the temperature of the heavy oil sample, $\eta$ is the viscosity, $T_{2LM}$ is the logarithmic mean of the $T_2$ distribution spectrum of the sample, and a, b, and c are non-zero constants. Typically, constant b has a value between 5 and 7 and constant c has a value between −0.7 and −0.5.

17 Claims, 4 Drawing Sheets

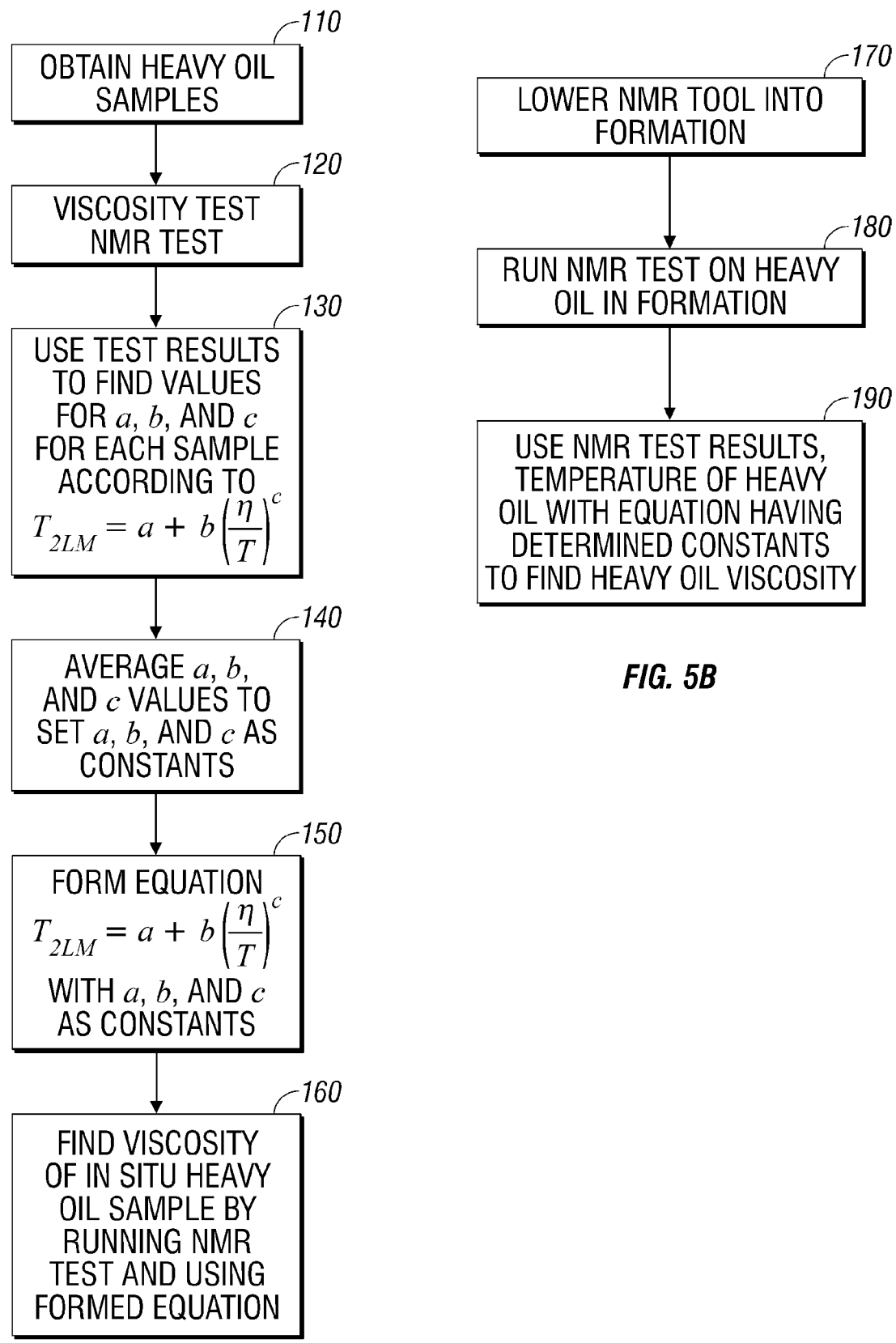

METHODS FOR DETERMINING IN SITU THE VISCOSITY OF HEAVY OIL

BACKGROUND OF THE INVENTION

1. Field of the Invention

This invention relates broadly to the investigation of geological formations. More particularly, this invention relates to in situ methods of determining the viscosity of heavy oils using nuclear magnetic resonance (NMR) techniques.

2. Description of Related Art

Most of the world's oil reservoirs contain heavy and viscous hydrocarbons which are difficult and costly to produce. Heavy oil viscosity is one of the few criteria available to determine production economics.

The use of NMR techniques has been known to provide a good correlation between viscosity and NMR relaxation time for relatively light oils. However, it fails for highly viscous oils (heavy oils).

More particularly, NMR relaxation time of bulk fluids is sensitive to the viscosity and temperature due to the dependence of rotational and translational correlation times of fluids. Presently in the petroleum industry, there are three widely used correlations between oil viscosity and the NMR logarithmic mean of the spin-spin relaxation time distribution:

$$T_{2LM} = \frac{1200}{\eta^{0.9}} \text{ (Straley-Kleinberg-Vinegar correlation)} \quad (1)$$

$$T_{2LM} = 7.13 \frac{T}{\eta} \text{ (Zega-Zhange correlation)} \quad (2)$$

$$T_{2LM} = 9.56 \frac{T}{\eta} \text{ (Lo correlation)} \quad (3)$$

where $\eta$ is the viscosity of the oil in centipoise (cp), T is the temperature in degrees Kelvin, and $T_{2LM}$ is the logarithmic mean of the $T_2$ distribution in milliseconds (mseconds). Unfortunately, as can be seen from FIG. 1 which plots the viscosity values measured in a lab (using a capillary viscometer) for heavy oil (HO) samples collected from different locations against the viscosities predicted by the correlations set forth above (using a 2 MHz Maran Ultra NMR instrument available from Oxford Instruments plc of Abingdon, Oxon, United Kingdom), none of these relationships correlated well.

BRIEF SUMMARY OF THE INVENTION

According to the invention, the viscosity of a heavy oil (i.e., an oil having a viscosity of 10 cp or greater at reservoir conditions) is determined according to an equation of the form $$T_{2LM} = a + b\left(\frac{\eta}{T}\right)^c \quad (4)$$

where a, b, and c are non-zero constants, constant b is set at between 5 and 7, and constant c is set at between −0.7 and −0.5. In a preferred aspect of the invention, constant b is set at 5.8±10% and constant c is set at −0.61±2%. In another preferred aspect of the invention, constant a is set less than one.

According to another aspect of the invention, the viscosity of a heavy oil sample is determined in situ in a formation by placing an NMR tool into a borehole in the formation, conducting an NMR experiment on the formation's heavy oil sufficient to generate a $T_2$ distribution spectrum, and, using the $T_2$ distribution spectrum obtained from the experiment, determining the viscosity of the heavy oil sample according to an equation of the form of equation (4) above.

Objects and advantages of the invention will become apparent to those skilled in the art upon reference to the detailed description taken in conjunction with the provided figures.

BRIEF DESCRIPTION OF THE DRAWINGS

FIG. 5A is a flow diagram of a method of one aspect of the invention.

FIG. 5B is a flow diagram of a method of another aspect of the invention.

DETAILED DESCRIPTION OF THE INVENTION

Figure 1:
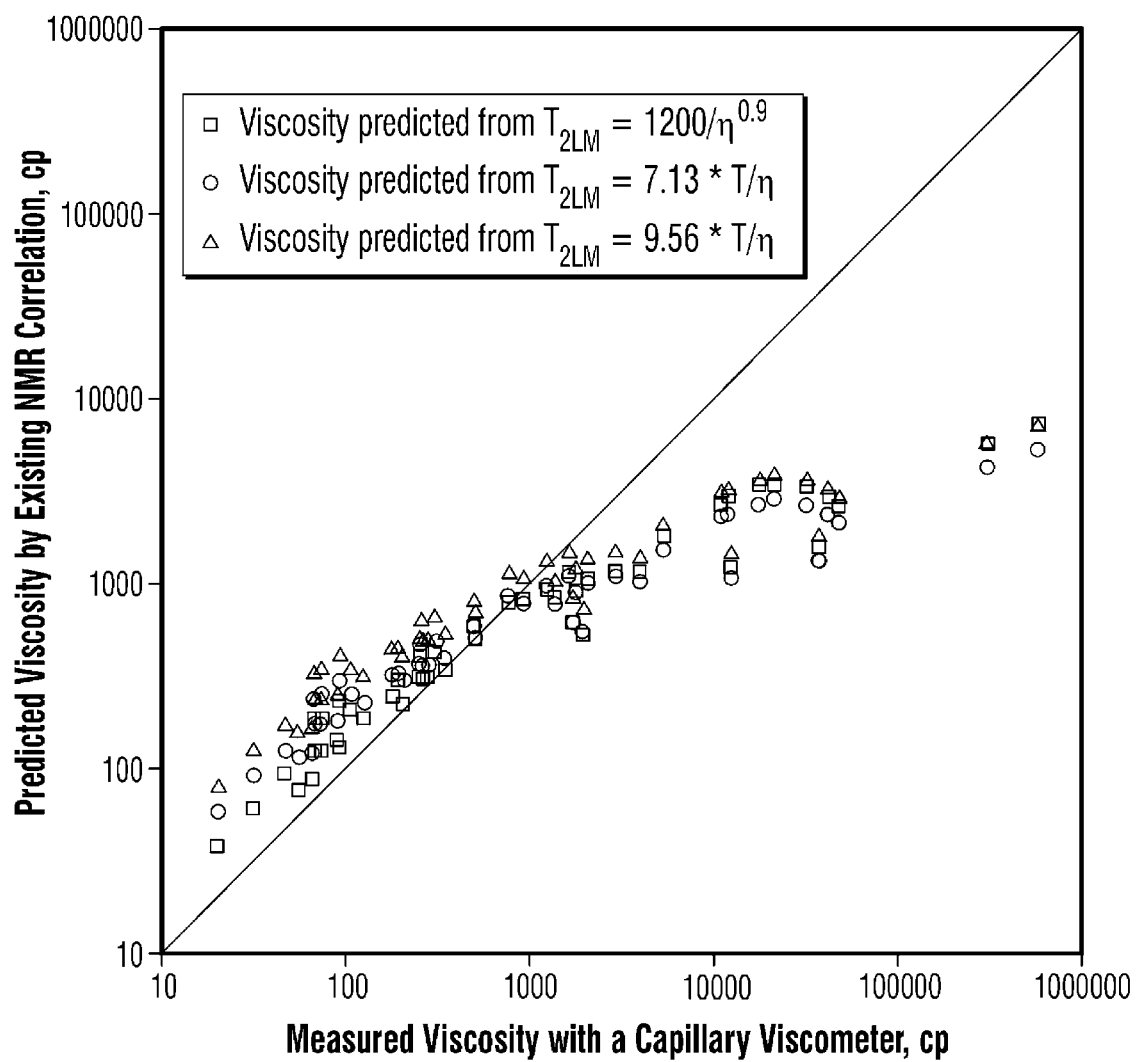
FIG. 1 is a double logarithmic plot showing predicted viscosities of heavy oil samples using prior art correlations versus the measured viscosities.

Before discussing the methods of the invention, a theoretical understanding is useful of how a relationship between viscosity and NMR test results can be generated.

Nuclear spin relaxation is a consequence of the coupling of the spin system to its surrounding, such as the lattice. Atoms and molecules are in a constant state of thermally activated motion. These motions in turn generate rapidly fluctuating magnetic and electric fields. It is these oscillating fields which provide a relaxation sink. Relaxation can occur via molecular rotation, translation, reorientation, etc.

Relaxation times depend on the nature of the coupling, of which there are many forms. Some of these are: dipole-dipole coupling, quadrapolar coupling, chemical shift coupling, scalar coupling, and spin-rotation interactions. Dipole-dipole coupling is the most commonly encountered coupling. It arises from the direct magnetic interactions of nuclear spins with each other. Quadrapolar coupling relates to the electric interaction of the spin $>\frac{1}{2}$ the nuclei with the surrounding electric fields. Chemical shift coupling relates to the indirect magnetic interaction of the external magnetic field and the nuclear spins, through the involvement of the electrons. Scalar coupling relates to the indirect magnetic interactions of nuclear spins with each other, through the involvement of the electrons. Finally, spin-rotation interactions relate to the interactions of the nuclear spins with magnetic fields generated by the rotation motion of the molecules. Generally for nuclei with I=½, where I is the spin quantum number, dipole-dipole coupling is the dominant source of the relaxation mechanism. Therefore, from a theoretical point of view, only the dipole-dipole coupling mechanism is considered.

To decipher the effects of the molecular motion on relaxation, the time dependence of the motion should be quantified. The autocorrelation function, $G(\tau)$, of a time dependent function, $F(t)$, is defined as $$G(\tau) = \langle F(t)F(t+\tau)\rangle \quad (5)$$

where $G(\tau)$ is the correlation between the function F at time t and at a later time t+τ, i.e., it describes how the value of the function depends on its previous values. Fourier transformation of the auto correlation functions gives the spectral densities, which describe the relative contributions of the Fourier components of the motion involved:

$$J(\omega) = \int_{-\infty}^{\infty} G(\tau)e^{i\omega\tau}\,d\tau \qquad (6)$$

where ω is a given frequency.

Typically, if the motional correlation time is $\tau_c$, the motions contain a spectrum of frequencies up to $\omega \sim 1/\tau_c$. The spectral density function gives the number of molecular motions at a given frequency, ω.

The relaxation rates $1/T_1$ (spin-lattice) and $1/T_2$ (spin-spin) for two identical spins are related to the spectral density functions by $$\frac{1}{T_1} = \frac{3}{2}\frac{\gamma^4 \hbar^2}{r^6} I(I+1)[J(\omega_0) + J(2\omega_0)] \qquad (7)$$

$$\frac{1}{T_2} = \frac{3}{8}\frac{\gamma^4 \hbar^2}{r^6} I(I+1)[J(0) + J(\omega_0) + J(2\omega_0)] \qquad (8)$$

where I is the spin quantum number, r is the distance between two spins of gyromagnetic ratio γ, ℏ is the Plank constant divided by 2π, and $\omega_0$ is the Larmor frequency.

According to Debye's theory, the autocorrelation function is normally expressed in terms of a single exponential decay as $$G(\tau)=\langle F(0)^2\rangle e^{-|\tau|/\tau_c} \qquad (9)$$

As a result, the relaxation rates of equations (7) and (8) become the following expressions (as set forth in Bloembergen, N. et al., "Relaxation Effects in Nuclear Magnetic Resonance Absorption", *Physical Review*, 73(7):679 (1948))

$$\frac{1}{T_1} = \frac{3}{10}\frac{\gamma^4 \hbar^2}{r^6}\left[\frac{\tau_c}{1+\omega_0^2\tau_0^2} + \frac{4\tau_c}{1+4\omega_0^2\tau_0^2}\right] \qquad (10)$$

$$\frac{1}{T_2} = \frac{3}{10}\frac{\gamma^4 \hbar^2}{r^6}\left[3\tau_c + \frac{5\tau_c}{1+\omega_0^2\tau_0^2} + \frac{2\tau_c}{1+4\omega_0^2\tau_0^2}\right] \qquad (11)$$

However, it is well known that molecular motion in many liquids cannot be expressed in a single exponential function. This has been shown to be true in a wide variety of materials, including organic liquids and solutions, polymers, and, in particular, many glass forming materials (supercooled liquids). For these materials, the time of molecular motion can last from $10^{-12}$ seconds to 100 seconds. The similar molecular dynamic behaviors have primarily been observed by three techniques: dielectric relaxation, photon correlation spectroscopy, and mechanical relaxation experiments.

Generally, in characterizing the macroscopic response, the correlation function $G(\tau)$ can be defined according to $$G(\tau)=\int\rho(\tau_c)71\,(\tau,\tau_c)d\tau_c \qquad (12)$$

where ρ(t) is the distribution of correlation times and $f(\tau,\tau_c)$ is the general expression of the decaying function. Two limiting scenarios are then known. The first scenario is that the non-exponential molecular dynamic behavior is due to a spatial distribution of simple molecular processes, each governed by an autocorrelation function which decays exponentially with a time constant, i.e., $f(\tau,\tau_c)=e^{-\tau/\tau_c}$. This corresponds to the fully heterogeneous limit which was considered by Nicot, B. et al., "A New Methodology for Better Viscosity Prediction Using NMR Relaxation", SPWLA 47th *Annual Logging Symposium*, (2006), which is considered by the Applicants to be inappropriate to providing a useful result. The second scenario assumes that all common molecular processes are characterized by the same autocorrelation function, but one with an inherently nonexponential decay. One such function is an empirical stretched-exponential function known as the Kohlrusch-Williams-Watts (KWW) function, where the autocorrelation is represented by a decay function of the form $$G(\tau)=\langle F(0)^2\rangle e^{-(\tau/\tau_c)^\beta} \qquad (13)$$

where β is the stretched exponent. As opposed to the fully heterogeneous limit considered by Nicot, B. et al., equation (13) presents the fully homogenous limit.

It is well known that there is no analytical expression for the Fourier transform of the KWW function. On the other hand, the Havriliak-Negami (HN) and Cole-Davidson (CD) functions have been extensively used to describe data from dielectric spectroscopies in the frequency domain. Although the HN and CD functions and the KWW function are not exactly Fourier transforms of each other, previous researchers have analyzed the close similarity of the KWW, HN, and CD functions. Therefore, it is believed that it is valid for the correlation function to be described by either the KWW or the HN or the CD model. Thus the spectral density can be expressed according to either $$J(\omega) = \frac{1}{\omega}\frac{\sin[\beta_{CD}\arctan(\omega\tau_c)]}{(1+\omega^2\tau_c^2)^{\beta_{CD}/2}} \qquad (14)$$

(Cole-Davidson model)

where $\beta_{CD}$ is the Cole-Davidson exponent, or $$J(\omega) = \frac{1}{\omega}\frac{\sin(\beta_{HN}\phi)}{\left\{1 + 2(\omega\tau_c)^{\alpha_{HN}}\sin\left[\frac{\pi}{2}(1-\alpha_{HN})\right] + (\omega\tau)^{2\alpha_{HN}}\right\}^{\beta_{HN}/2}} \qquad (15)$$

(Havriliak-Negami model)
where $$\phi = \arctan\left|\frac{(\omega\tau_c)^{\alpha_{HN}}\cos\left[\frac{\pi}{2}(1-\alpha_{HN})\right]}{1+(\omega\tau_c)^{\alpha_{HN}}\sin\left[\frac{\pi}{2}(1-\alpha_{HN})\right]}\right| \qquad (16)$$

and where $\alpha_{HN}$ and $\beta_{HN}$ are the Havriliak-Negami exponents, which characterize an asymmetrical and symmetrical broadening of the spectral density, respectively.

For the intermediate case (i.e., not fully heterogenous or fully homogenous), the correlation function can be expressed as $$G(\tau) = \int \rho_{\gamma_{in}}(\tau_c)\exp\left[-\left(\frac{\tau}{\tau_c}\right)^{\beta_{in}}\right]d\tau_c \qquad (17)$$

where $\beta_{in}$ is the stretched exponent in the intermediate case. Using equation (17), a non-exponential correlation function $G(\tau)$ may be defined where $0<\beta<1$ and $\beta \leq \beta_{in} \leq 1$ with a degree of heterogeneity $h=(\beta_{in}-\beta)/(1-\beta)$. This quantity is chosen such that it vanishes in the homogeneous extreme and it is unity in the heterogeneous limit. See, Bohmer, R. et al. "Nature of the Non-Exponential Primary Relaxation in Structural Glass-Formers Probed by Dynamically Selective Experiments", *Journal of Non-Crystalline Solids*, 235-237:1 (1998).

Molecular motion in liquids is often compared to the prediction of the Debye-Stokes-Einstein (DSE) equation. The equation describes the rotational motion of a sphere of radius r in the hydrodynamic continuum with viscosity $\eta$ and temperature T. The DSE equation predicts the rotational correlation time $\tau_c$ to be $$\tau_c = \frac{4\pi\eta r^3}{3kT} \quad (18)$$

where k is the Boltzmann constant. Although this theory was not initially designed for complex molecules, as set forth in Blackburn, F. R. et al., "Translational and Rotational Motion of Probes in Supercooled 1,3,5-Tris(naphthyl)benzene, *Journal of Physical Chemistry*, 100: 18249 (1996), the experimental observation of molecular rotation followed the temperature dependence of the DSE equation as the viscosity was changed by twelve orders of magnitude. Therefore, the DSE relation is assumed to be valid for a very wide range of viscosity and temperature.

In linking NMR measurements such as $T_2$ to viscosity, they should be linked to the correlation time $\tau_c$. According to Bloembergen, N. et al., "Relaxation Effects in Nuclear Magnetic Resonance Absorption", *Physical Review*, 73(7):679 (1948), in the extreme narrow limit ($\omega\tau_c \ll 1$) and the long correlation time ($\omega\tau_c \gg 1$), $T_2$ is inversely proportional to the correlation time;

$$T_2 \sim 1/\tau_c. \quad (19)$$

Given that the logarithmic mean of the $T_2$ distribution is given by $$T_{2LM} = \left(\prod_{i=1}^{n} T_{2i}^{n_i}\right)^{\frac{1}{\sum_i n_i}}, \text{ or} \quad (20)$$

$$\ln(T_{2LM}) = \frac{\sum_i n_i \ln(T_{2i})}{\sum_i n_i}$$

where $n_i$ is the mole of proton corresponding to the i-th component with $T_2$ relaxation time in $T_2$ distribution spectrum, the inverse relationship of $T_2$ and the correlation time can be used to rewrite equation (20) according to $$T_{2LM} \sim \left(\prod_{i=1}^{n} \tau_{c,i}^{-n_i}\right)^{\frac{1}{\sum_i n_i}} \quad (21)$$

where $\tau_{c,i}$ is the constituent correlation time corresponding to $T_{2,i}$ of the i-th molecular constituent.

Without loss of generality, it may be assumed that there are L components of a (heavy oil) mixture in the extreme narrow limit region and n-L components in the very long correlation time region. The constituent correlation times $\tau_{c,i}$ can be expressed as the following linear relationship in terms of the characteristic correlation time $\tau_c$ of the mixture:

$$\tau_{c,1}=k_1\tau_c, \tau_{c,2}=k_2\tau_c, \tau_{c,3}=k_3\tau_c, \ldots \tau_{c,n}=k_n\tau_c \quad (22)$$

where $k_i$ is the ratio between the correlation time of constituent i and the characteristic correlation time of the mixture, $$\frac{\tau_{c,i}}{\tau_c}.$$

Substituting equation (22) into equation (21) yields:

$$T_{2LM} \sim \left(\prod_{i=1}^{n}(k_i\tau_c)^{-n_i}\right)^{\frac{1}{\sum_i n_i}} = \frac{1}{\tau_c}\left(\prod_{i=1}^{n}(k_i^{-n_i})\right)^{\frac{1}{\sum_i n_i}} \quad (23)$$

The Applicants have determined that the heavy oil viscosity-temperature behavior can be predicted by the models used for supercooled liquids. Therefore, the Applicants believe that the stretch-exponential function should be used as the correlation function for heavy oil systems. According to the CD and HN models described above with reference to equations (14) and (15), it can be found that $T_2$ follows the law according to equation (19). However, according to Dries, Th., et al., "$^2$H-NMR Study of the Glass Transition in Supercooled Ortho-terphenyl", *Journal of Chemical Physics*, 88(5): 2139 (1988), at the long correlation time region ($\omega\tau_c \gg 1$), $T_2$ is proportional to $\tau_c$; i.e., $T_2 \sim \tau_c$. Therefore, according to the CD and HN models, equation (20) becomes the following $$T_{2LM} \sim \left[\frac{\left(\prod_{i=1}^{L}(k_i\tau_c)^{-n_i}\right)}{\left(\prod_{i=L+1}^{n}(k_i\tau_c)^{n_i}\right)}\right]^{\frac{1}{\sum_i n_i}} = \tau_c^{\Delta}\left[\frac{\left(\prod_{i=1}^{L}(k_i^{-n_i})\right)}{\left(\prod_{i=L+1}^{n}(k_i^{n_i})\right)}\right]^{\frac{1}{\sum_i n_i}} \quad (24)$$

where $$\Delta = \frac{\sum_{i=L+1}^{n} n_i - \sum_{i=1}^{L} n_i}{\sum_i n_i}.$$

It can be found from equation (24) that $T_{2LM}$ is proportional to $\tau_c^{\Delta}$. Combining with equation 18, the following power law correlation equation (previously set forth as equation (4) above) can be constructed to link $T_{2LM}$ and $\eta/T$ in heavy oil samples:

$$T_{2LM} = a + b\left(\frac{\eta}{T}\right)^c \quad (25)$$

where a, b, and c, are non-zero constants, and where, as will be discussed hereinafter, c is typically set at between −0.7 and −0.5. In the power law correlation equation (25), constant a relates to data acquisition parameters, but is constant for a given experimental setting. Constants b and c are physical/chemical constants that characterize the molecular motion of the heavy oil and which are constants for materials which share similar physical-chemical properties. Thus, given constants a, b, and c, the viscosity of a heavy oil sample can be determined by measuring the temperature of the sample and conducting an NMR test of the sample to determine the logarithmic mean of its $T_2$ distribution. It is noted that equation (25) can be reduced to equations (2) and (3) which govern light oil if constant c is set to −1, and constant a is set to 0.

Given the above understanding of how the viscosity of heavy oil can be determined from NMR test results, fourteen heavy oil samples were collected from different regions of the world. Their viscosities at different temperatures were measured with a capillary viscometer.

Figure 2:
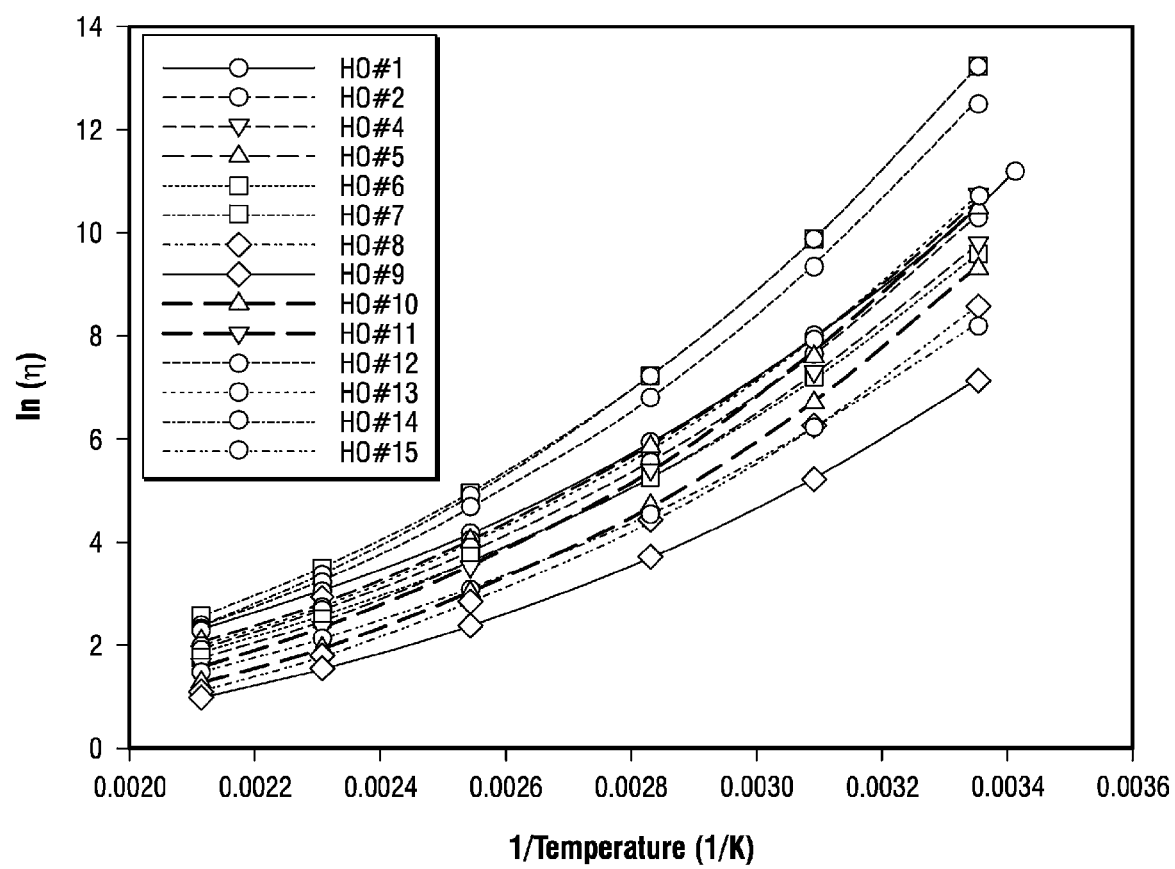
FIG. 2 is a graph showing the relationship between the viscosity and temperature of fourteen different heavy oil samples.

FIG. 2 is a graph showing the relationship between the viscosity and temperature of the fourteen different heavy oil samples. FIG. 2 graphs the natural log of the viscosity of the heavy oil samples against the inverse of the Kelvin temperature at which the viscosity data was obtained.

Three of the fourteen heavy oil samples (heavy oil samples 2, 7, and 8 representing average heavy, extremely heavy, and "lighter" heavy oils) were then pressed into temperature controlled ceramic tubes for nuclear magnetic resonance testing. NMR experiments were conducted at a Larmor frequency of 2 MHz on a Maran Ultra NMR instrument. Proton spin-lattice relaxation time ($T_1$) was measured at 10, 15, 25, 50, 80 and 100° C. by the saturation recovery technique. Proton spin-spin relaxation times ($T_2$) were determined at the above-stated temperatures, and a modified Carr-Purcell-Gill-Meiboom (CPGM) sequence ($\pi/2$-$\tau$-$\pi$-$\tau$-echoes-$5T_1$-$\pi/2$-$\tau$-$\pi$-$\tau$-echoes-$5T_1$) was used with $\tau=100$ μs and a cycle time greater than 5 times $T_1$. The $T_2$ distribution spectrum was recovered by the inverse Laplace transform of time domain CPGM echo signals. The logarithmic mean of the $T_2$ distribution ($T_{2LM}$) was determined according to equation (20) above.

Using the $T_{2LM}$ determinations for heavy oil samples #2, #7 and #8 at the different temperatures and the viscosity determinations of Table 1 at the same temperatures, values for a, b, and c were obtained via a fitting algorithm such as the least squares algorithm in order to fit the data to equation (25). The best fit values and the coefficient of determination ($R^2$) were determined as set forth in Table 1:

TABLE 1

| HO Sample | a | b | c | $R^2$ |
|---|---|---|---|---|
| HO#2 | 0.4070 | 6.2053 | −0.6160 | 0.998 |
| HO#7 | 0.3426 | 5.4494 | −0.6063 | 0.998 |
| HO#8 | 0.3550 | 5.8159 | −0.6193 | 0.998 |
| Average | 0.3682 | 5.8235 | −0.6139 | |

Figure 3:
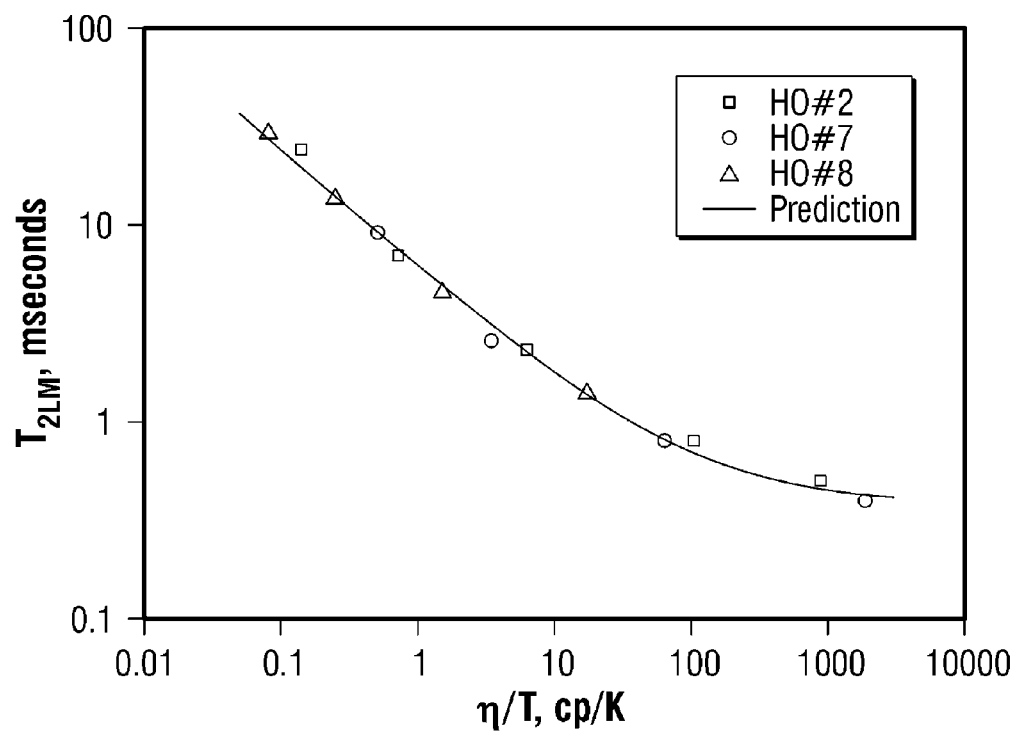
FIG. 3 is a double logarithmic plot showing a curve utilizing the form of equation (4) having constants obtained from averaging the data from three heavy oil samples.

FIG. 3 shows the data of Table 1 as a double logarithmic plot where the solid line curve represents the correlation according to equations (4) and (25) using the average values of a, b, and c of the three heavy oil samples. The thirteen data points are the viscosity and and $T_{2LM}$ values of heavy oil sample #2 at 10, 25, 50, 80 and 110° C., and for heavy oil samples #7 and #8 at 25, 50, 80 and 110° C.

Figure 4:
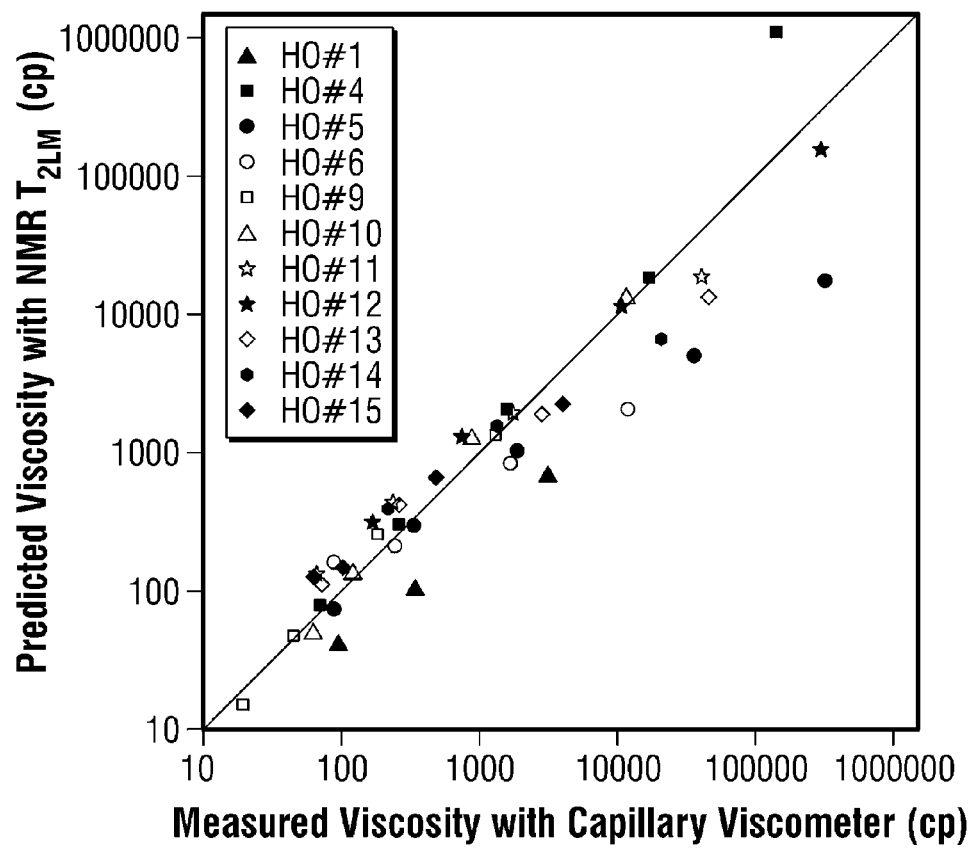
FIG. 4 is a plot comparing the viscosities of eleven heavy oils as measured in the lab and as calculated according to equation (4) using the constants obtained from the samples of FIG. 3.

In order to test the integrity of the determination of constants a, b, and c, i.e., the average values set forth in Table 1, NMR measurements were taken of the remaining eleven heavy oil samples in the manner discussed above with reference to the first three oil samples. Using the resulting $T_{2LM}$ determinations and equation (4) or (25) with the constants a, b, and c set to 0.3682, 5.8235, and −0.6139 respectively, predicted (calculated) viscosity measurements for the eleven samples were made for the various temperatures. FIG. 4 is a double logarithmic plot comparing the viscosities of the eleven heavy oils as measured in the lab and as calculated. FIG. 4 shows that using the provided constants, equation (4) or (25) provides a relatively good estimation of the viscosity based on the NMR determinations;

$$\log STDDev = \exp\left(\sqrt{\frac{\sum_{i}^{n}(\ln(\eta_{NMR}) - \ln(\eta_{viscometer}))^2}{n-1}}\right)$$

$$= 2.67, \text{ particularly}$$

when compared with the prior art results shown in FIG. 1.

Turning now to FIG. 5A, a flow diagram of a method in accord with an aspect of the invention is shown. As shown in FIG. 5A, at step 110, a plurality of samples of heavy oil are obtained. The samples may be obtained from a single formation or from multiple formations. The samples are then subjected at 120 to viscosity and NMR tests to obtain viscosity measurements and $T_{2LM}$ determinations. The viscosity and NMR tests are preferably conducted at multiple temperatures. At 130, using the results from the viscosity and NMR tests, and using equation (4), a fitting algorithm is used to obtain values for variables a, b, and c for each of the plurality of samples which were tested. A preferred fitting algorithm is the least squares algorithm. Then, at 140, an average of the values for each of a, b, and c can be taken. At 150, an equation of the form of equation (4) is generated using the average values as constants; e.g., $$T_{2LM} = 0.3682 + 5.8235\left(\frac{\eta}{T}\right)^{-0.6139}.$$

Depending upon the number of samples obtained and tested, if desired, the variables for samples having one or more outlier values for a, b, and c can be discarded prior to averaging the variables in generating the constants. Once the equation is formulated, according to a further aspect of the invention, at 160, the equation can be used to provide estimated or calculated values of viscosity for one or more additional heavy oil samples which have been subjected to NMR testing.

According to another aspect of the invention, a, b, and c are non-zero constants. Preferably, constant b is between 5 and 7, and constant c is set at between −0.7 and −0.5. Also, constant a is preferably set to be less than 1. More preferably, constant b is 5.8±10% and constant c is 0.61±2%. Most preferably, a=0.3682, b=5.8235, and c=−0.6139.

Turning now to FIG. 5B, a flow diagram in accord with another aspect of the invention is seen. At 160, an NMR logging tool is lowered in a borehole traversing a formation. The logging tool may be any tool capable of making $T_2$ measurements of oil in the formation such as CMR-Plus and MR Scanner, both available from Schlumberger Technology Corporation of Sugar Land, Tex., USA. At 170, an oil sample at a location in the formation is subjected to testing by the NMR logging tool. At 180, using the results of the testing, a determination of a $T_{2LM}$ value is made for that sample. Then, at 190, using the $T_{2LM}$ value, the temperature of the sample, and an equation of the form of equation (4), and having predetermined constants a, b, and c as previously described, a determination (estimation) of the viscosity of the oil sample is made by plugging the $T_{2LM}$ value and the temperature of the sample into the equation and solving for the viscosity. Steps 170, 180, and 190 may be repeated for any number of oil samples in the formation. The method of FIG. 5B is particularly useful for determining in situ the viscosity of heavy oils in a formation.

A borehole tool for implementing the method of FIG. 5B is described in U.S. Pat. No. 6,246,236, which is incorporated herein by reference.

There have been described and illustrated herein several embodiments of a method of determining in situ the viscosity of heavy oils. While particular embodiments of the invention have been described, it is not intended that the invention be limited thereto, as it is intended that the invention be as broad in scope as the art will allow and that the specification be read likewise. Thus, while it was disclosed that a particular number (three) of oil samples were used to generate constants for the power law correlation equation, it will be appreciated that other numbers of samples could be utilized. Also, while a particular NMR tool was described for carrying out the methods, it will be understood that other tools could be used, provided the tool is capable of generating a determination of the $T_2$ distribution. It will therefore be appreciated by those skilled in the art that yet other modifications could be made to the provided invention without deviating from its scope as claimed.

What is claimed is:

1. A method for determining the viscosity of a heavy oil located in a formation traversed by a borehole, comprising:
   locating a nuclear magnetic resonance (NMR) logging tool in the borehole;
   making $T_2$ measurements of the heavy oil in situ; and
   without bringing said heavy oil uphole, determining the viscosity η of the heavy oil according to an equation of the form $$T_{2LM} = a + b\left(\frac{\eta}{T}\right)^c,$$

where T is the temperature of the heavy oil, $T_{2LM}$ is the logarithmic mean of the $T_2$ distribution spectrum of the sample obtainable from said $T_2$ measurements, and a, b, and c are non-zero constants.

2. A method according to claim 1, wherein b is between 5 and 7, and c is between −0.7 and −0.5.

3. A method according to claim 2, wherein a is less than 1.

4. A method according to claim 2, wherein b is 5.8±10% and c is −0.61±2%.

5. A method according to claim 1, further comprising moving said NMR logging tool in the borehole, wherein making $T_2$ measurements of the heavy oil comprises making $T_2$ measurements of multiple samples of heavy oil, and determining the viscosity η of the heavy oil comprises determining the viscosities of the multiple samples of heavy oil.

6. A method according to claim 1, further comprising measuring the temperature T of the heavy oil and using the measured temperature in determining the viscosity η of the heavy oil according to said equation.

7. A method according to claim 1, further comprising:
   prior to locating an NMR logging tool in the borehole, obtaining a plurality of samples of heavy oil from at least one formation;
   testing said plurality of samples of heavy oil in a laboratory to obtain viscosity and $T_2$ NMR measurements for each of said plurality of samples;
   using said equation and said viscosity and $T_2$ NMR measurements, obtaining proposed values for a, b, and c as variables for each of said plurality of samples of heavy oil; and
   using said proposed values, determining a, b, and c as said non-zero constants.

8. A method according to claim 7, wherein said testing is done at a plurality of temperatures.

9. A method according to claim 8, wherein obtaining proposed values for a, b, and c comprises using a least squares fitting technique.

10. A method according to claim 8, wherein determining a, b, and c as said non-zero constants comprises averaging said proposed values for a, b, and c as variables to obtain said non-zero constants.

11. A method for determining the viscosity of a heavy oil located in a formation traversed by a borehole, comprising:
   obtaining a plurality of samples of heavy oil from at least one formation;
   testing said plurality of samples of heavy oil in a laboratory to obtain viscosity and $T_2$ nuclear magnetic resonance (NMR) measurements for each of said plurality of samples;
   using said viscosity and $T_2$ NMR measurements, and an equation of the form $$T_{2LM} = a + b\left(\frac{\eta}{T}\right)^c,$$

where η is the viscosity of the heavy oil tested, T is the temperature of the heavy oil tested, $T_{2LM}$ is the logarithmic mean of the $T_2$ distribution spectrum of the heavy oil tested obtainable from said $T_2$ NMR measurements, and a, b, and c are non-zero values, to obtain proposed values for a, b, and c for each of said plurality of samples of heavy oil;
   using said proposed values, determining a, b, and c as non-zero constants; and
   without bringing said heavy oil located in the formation uphole, determining the viscosity η of that heavy oil by obtaining $T_2$ NMR measurements of that heavy oil, and using said $T_2$ NMR measurements of that heavy oil, the temperature T of that heavy oil, and said equation with said non-zero constants and solving for the viscosity of that heavy oil.

12. A method according to claim 11, wherein b is between 5 and 7, and c is between −0.7 and −0.5.

13. A method according to claim 12, wherein a is less than 1.

14. A method according to claim 12, wherein b is 5.8±10% and c is −0.61±2%.

15. A method according to claim 11, wherein said testing is done at a plurality of temperatures.

16. A method according to claim 15, wherein obtaining proposed values for a, b, and c comprises using a least squares fitting technique.

17. A method according to claim 15, wherein determining a, b, and c as non-zero constants comprises averaging said proposed values for a, b, and c to obtain said non-zero constants.

* * * * *